United States Patent
Prentice et al.

(10) Patent No.: US 8,809,049 B2
(45) Date of Patent: Aug. 19, 2014

(54) METHODS FOR PRODUCING MAMMALIAN CELLS

(75) Inventors: Holly Prentice, Carlisle, MA (US); Barbara Ehrenfels, Chelmsford, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 1828 days.

(21) Appl. No.: 11/667,927

(22) PCT Filed: Nov. 21, 2005

(86) PCT No.: PCT/US2005/042182
§ 371 (c)(1),
(2), (4) Date: Dec. 13, 2007

(87) PCT Pub. No.: WO2006/055915
PCT Pub. Date: May 26, 2006

(65) Prior Publication Data
US 2008/0131929 A1 Jun. 5, 2008

Related U.S. Application Data

(60) Provisional application No. 60/629,319, filed on Nov. 19, 2004.

(51) Int. Cl.
*C12N 15/85* (2006.01)
*C12N 5/00* (2006.01)

(52) U.S. Cl.
CPC .......... *C12N 5/0031* (2013.01); *C12N 2500/20* (2013.01); *C12N 2510/02* (2013.01)
USPC .......................................... 435/325; 435/69.1

(58) Field of Classification Search
None
See application file for complete search history.

(56) References Cited

U.S. PATENT DOCUMENTS

| | | | |
|---|---|---|---|
| 5,122,469 A | 6/1992 | Mather et al. | |
| 5,156,956 A | 10/1992 | Motoki et al. | |
| 2007/0161079 A1* | 7/2007 | Reiter et al. | 435/69.1 |
| 2008/0057584 A1* | 3/2008 | Sandig et al. | 435/455 |

FOREIGN PATENT DOCUMENTS

WO  WO 95/12664  5/1995

OTHER PUBLICATIONS

Morris and Schmid, "Effects of Insulin and LongR3 on Serum-Free Chinese Hamster Ovary Cell Cultures Expressing Two Recombinant Proteins", Biotechnol. Prog. 16: 693-697 (2000).*
Chu et al., "Industrial choices for protein production by large-scale cell culture," *Current Opinion in Biotechnology*, 12(2):180-187 (2001).
International Preliminary Report on Patentability in PCT/US2005/042182 (filed Nov. 21, 2005); 6 pages.
International Search Report in PCT/US2005/042182 (filed Nov. 21, 2005); 6 pages.
Matsumura et al., "Adaptation of hybridoma cells to higher ammonia concentration," *Cytotechnology* 7:103-112 (1991).
Newland et al., "Ammonia inhibition of hybridomas propagated in batch, fedbatch, and continuous culture," *Biotechnology and Bioengineering*, 43:434-438 (Feb. 19, 2004).
Rasmussen et al., "Isolation, characterization and recombinant protein expression in Veggie-CHO: A serum-free CHO host cell line," *Cytotechnology*, 28:31-42 (1998).
Renner et al., "Recombinant Cyclin E Expression Activates Proliferation and Obviates Surface Attachment of Chinese Hamster Ovary (CHO) Cells in Protein-Free Medium," *Biotechnology and Bioengineering*, 47:476-482 (1995).
Sinacore at al., "Adaptation of Mammalian Cells to Growth in Serum-Free Media," *Molecular Biotechnology*, 15:249-257 (2000).
Supplementary European Search Report in EP 05851941 based on PCT/US2005/042182 (filed Nov. 21, 2005); 7 pages.
Written Opinion of the International Searching Authority in PCT/US2005/042182 (filed Nov. 21, 2005); 5 pages.
Zang et al., "Production of Recombinant Proteins in Chinese Hamster Ovary Cells Using a Protein-Free Cell Culture Medium," *Biotechnology*, 13:389-392 (1995).

* cited by examiner

*Primary Examiner* — Anand Desai
(74) *Attorney, Agent, or Firm* — Sterne, Kessler, Goldstein & Fox P.L.L.C.

(57) ABSTRACT

The invention relates to methods for producing mammalian cells having enhanced characteristics such as faster growth rates and the ability to grow to higher cell densities. The invention also relates to methods for producing cells having the ability to grow in media lacking components such as insulin and insulin substitutes. The invention also relates to isolated mammalian cells having improved growth characteristics and/or the ability to grow in media lacking components such as insulin and insulin substitutes.

67 Claims, 5 Drawing Sheets

METHODS FOR PRODUCING MAMMALIAN CELLS

BACKGROUND OF THE INVENTION

1. Field of the Invention

The present invention relates to the production of mammalian cell lines having enhanced growth characteristics that can be used for high level production of recombinant proteins and other cellular products.

2. Related Art

Mammalian cells are often used as hosts for the production of recombinant proteins. A goal in industrial settings is to produce the maximum amount of recombinant protein in the shortest amount of time while minimizing costs. Various general strategies can be employed to increase recombinant protein yield from mammalian cells. In general, total protein yield can be increased by increasing the number of protein producing cells that are grown in a given time period. One strategy to increase the number of cells obtained is to increase the size of the culture. The use of bioreactors in industrial settings allows for substantially increased culture volumes as compared to ordinary laboratory culture conditions. Increasing culture volume, however, entails significant increases in equipment and media costs.

Another strategy to improve recombinant protein yield from mammalian cells is to improve the growth characteristics of the cells that are used to produce the protein. For example, cells that grow faster and/or that grow to higher density in culture and/or maintain viability for longer periods of time in culture, as compared to mammalian host cells commonly used in industrial protein production, would facilitate higher protein yields. Improved growth of cells can potentially be achieved by optimizing the culture medium used. However, optimizing culture media is expensive, and the inherent characteristics of the cells may limit the amount of cells that can be obtained regardless of improvements in the media.

The cost of industrial-scale recombinant protein production is highly dependent on the ingredients used in culture media. Serum is an ingredient traditionally included in cell culture medium formulations. Although serum can provide factors needed for cell growth in culture, serum is an expensive and undefined component. The proteins and other substances found in serum can interfere with the isolation and purification of proteins produced by cells grown in serum-containing media. In addition, the use of serum in culture media for the production of biopharmaceutical products raises several safety and regulatory concerns. The use of serum increases the possibility of introducing contaminating factors, such as viruses and transmissible protein factors, into the culture medium. The use of serum is therefore discouraged by regulatory authorities. Thus, serum-free culture conditions are highly preferred, and are sometimes necessary, for the production of recombinant proteins from mammalian cells.

In order to grow mammalian cells in serum-free conditions, however, it is necessary to include various ingredients that take the place of serum in the culture medium. The most expensive ingredient in serum-free media is typically insulin. Although insulin substitutes are known and available, such substitutes are equally expensive, if not more expensive than insulin itself.

In view of the foregoing factors and considerations, it is clear that there is a need in the art for improving protein yields from mammalian cells at reasonable cost.

SUMMARY OF THE INVENTION

The present invention addresses the aforementioned need in the art by providing methods for producing mammalian cells having enhanced growth characteristics and/or the ability to grow in media that lacks insulin and insulin substitutes.

According to one aspect of the invention, methods are provided for producing one or more mammalian cells having enhanced growth characteristics. The methods according to this aspect of the invention comprise: (a) subjecting either (i) a starting population of mammalian cells, or (ii) one or more cells obtained in step (b), to selective conditions in which less than 70% of the starting population of cells remain viable; and (b) obtaining one or more mammalian cells that remain viable under the selective conditions. The cells obtained from the selection cycles exhibit an integral cell area (ICA) that is at least 25% greater than the corresponding ICA of the starting population of cells when the cells obtained from the selection cycles and the starting population of cells are grown under substantially the same culture conditions. Exemplary selective conditions, according to this aspect of the invention, comprise incubating the cells (either the starting population of cells or the cells obtained from the selection cycles) in a bioreactor.

The basis for this aspect of the invention is the observation that cell viability drops for cells grown in a batch or fed-batch bioreactor. Thus, the bioreactor environment can provide selective pressures that produce cells with enhanced growth characteristics. The use of a bioreactor to select for cells having enhanced growth characteristics may be referred to generally herein as "bioreactor evolution."

According to another aspect of the invention, methods are provided for producing one or more mammalian cells having the ability to grow in media lacking or substantially lacking insulin and insulin substitutes. The methods according to this aspect of the invention comprise: (a) contacting either (i) a starting population of mammalian cells that are unable to grow in insulin-free media (e.g., mammalian cells that exhibit an average growth rate of less than 0.20 $day^{-1}$ in media lacking or substantially lacking insulin and insulin substitutes), or (ii) one or more cells obtained in step (b), with a culture medium lacking or substantially lacking insulin and insulin substitutes; and (b) obtaining one or more cells that remain viable in the medium lacking or substantially lacking insulin and insulin substitutes. The cells obtained from the selection cycles have a growth rate of at least 0.30 $day^{-1}$ in a medium lacking or substantially lacking insulin and insulin substitutes.

According to another aspect of the invention, methods are provided for producing one or more mammalian cells having the ability to grow in media lacking or substantially lacking insulin and insulin substitutes. The methods according to this aspect of the invention comprise performing two separate, sequential selection procedures, each selection procedure comprising or more selection cycles. The first selection procedure comprises one or more first selection cycles, wherein each first selection cycle comprises: (a) subjecting either (i) a starting population of mammalian cells, or (ii) one or more cells obtained in step (b), to selective conditions in which less than 70% of the starting population of cells remain viable; and (b) obtaining one or more mammalian cells that remain viable under the selective conditions. The second selection procedure comprises one or more second selection cycles, wherein each second selection cycle comprises: (c) contacting either (i) one or more cells obtained from the one or more first selection cycles, or (ii) one or more cells obtained in step (d), with a culture medium lacking or substantially lacking insulin and insulin substitutes; and (d) obtaining one or more cells that remain viable in the medium lacking or substantially lacking insulin and insulin substitutes. The cells obtained from the second selection cycles have a growth rate of at least 0.30 day$^{-1}$ in a medium lacking or substantially lacking insulin and insulin substitutes.

According to another aspect of the invention, mammalian cells are provided having enhanced growth characteristics. For example, this aspect of the invention provides one or more isolated CHO cells that exhibit an integral cell area (ICA) that is at least 25% greater than the corresponding ICA of control cells such as, e.g., DG44 CHO cells, when the isolated CHO cells and the control cells are grown under substantially the same culture conditions. This aspect of the invention also provides one or more isolated CHO cells that, when incubated in a medium lacking or substantially lacking insulin and insulin substitutes, exhibit an ICA that is at least 25% greater than the corresponding ICA of control cells such as, e.g., DG44 CHO cells incubated in a medium lacking or substantially lacking insulin and insulin substitutes. This aspect of the invention also provides mammalian cells having enhanced growth characteristics, wherein the cells are obtained using any of the methods of the invention described elsewhere herein.

According to another aspect of the invention, methods are provided for producing polypeptides. The methods according to this aspect of the invention comprise: (a) introducing a nucleic acid molecule encoding the polypeptide into one or more isolated cells; and (b) culturing the cells containing the nucleic acid molecule under conditions in which the polypeptide is expressed from the nucleic acid molecule. In the methods according to this aspect of the invention, the cells into which the nucleic acid molecule is introduced are: (1) any cells of the invention described elsewhere herein, and (2) any cells obtained using any of the methods of the invention described elsewhere herein.

DETAILED DESCRIPTION OF THE INVENTION

Enhanced Growth Characteristics

Figure 1:
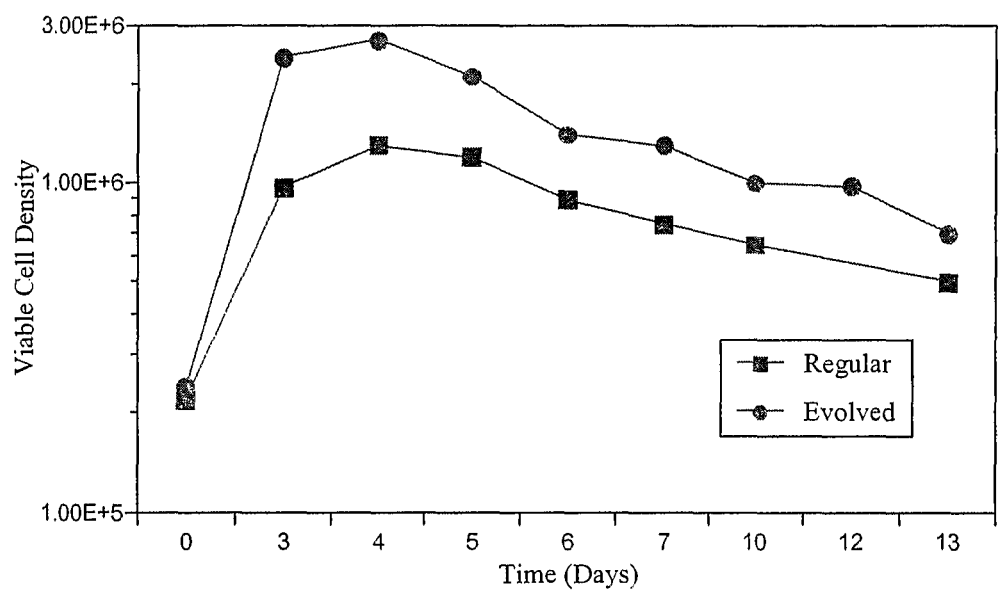
FIG. 1 is a graph showing the viable cell density of the control cell line (SF DG44="regular") and the viable cell density of the cell line obtained from the bioreactor evolution process (DG44(E)="evolved"), as a function of time in a fed-batch process. The ten-day ICA of the "regular" cells is 7.84×10$^6$. The ten-day ICA of the "evolved" cells is 1.43× 10$^7$. The "evolved" cells attained a 107% increase in peak cell density and an 82% increase in ICA as compared to the "regular" cells.

The present invention includes methods for producing one or more mammalian cells having enhanced growth characteristics. The invention also includes mammalian cells having enhanced growth characteristics. As used herein, the expression "mammalian cell having enhanced growth characteristics" means a mammalian cell that exhibits: (i) a faster growth rate, and/or (ii) the ability to achieve a higher cell density, and/or (iii) the ability to remain viable for a longer period of time, as compared to a reference cell or population of cells that are subjected to substantially the same culture conditions.

Certain aspects of the invention comprise subjecting a starting population of cells to one or more selection cycles. The selection cycles can, in certain instances, comprise subjecting cells to selective conditions, e.g., conditions in which less than 70% of the starting population of cells remain viable. The cells obtained from the selection cycles can exhibit one or more enhanced growth characteristics compared to a reference cell or population of cells. The reference cell or population of cells can be the starting population of cells used in the methods of the invention.

In other aspects, the cells of the invention have enhanced growth characteristics relative to a reference cell or cell line that is known in the art. An exemplary reference cell line that is known in the art is the CHO cell line designated DG44 (Urlaub et al., *Somatic Cell and Molecular Genetics* 12:555-566 (1968)). DG44 cells are commercially available from, e.g., Invitrogen Corporation, Carlsbad, Calif. Other known and available cells can be used as reference cells in the context of the present invention.

Persons of ordinary skill in the art would readily appreciate how to determine whether a given cell has enhanced growth characteristics as this term is used in the context of the present invention. For example, to determine if a given cell (e.g., one produced by the methods of the invention) has enhanced growth characteristics, one skilled in the art could measure the growth rate and/or the cell density obtained when the cell is subjected to a defined set of culture conditions, and compare these values to the growth rate and/or cell density obtained with a reference cell that has been subjected to the same or substantially the same defined set of culture conditions. In certain instances, in order to determine if a given cell has enhanced growth characteristics relative to a reference cell, the cell and the reference cell are grown in the absence of selective conditions, e.g., in the absence of the selective conditions that were used in the selection cycles of the methods of the invention. If the values obtained from the cell produced by the method of the invention are greater than the values obtained from the reference cell, then the cell produced by the method of the invention has "enhanced growth characteristics."

The expression "enhanced growth characteristics" can also be expressed in terms of "integral cell area" (ICA). ICA is calculated as follows:

$$ICA = \text{\# days} \times [(\text{final cell density} - \text{initial cell density})/\ln(\text{final cell density/initial cell density})].$$

In the equation above, "# days" refers to the number of days the cells are incubated in culture, at which point "final cell density" is measured. The "initial cell density" is the density of cells in culture at the beginning of the culture period. The ICA can be expressed in terms of "X-day ICA." For instance, if the cells are incubated in culture for ten days, the ICA may be expressed as the "ten-day ICA." Where the ICA of a "test" cell is greater than the ICA of a reference cell grown under the same or substantially the same culture conditions, the "test" cell is regarded as having "enhanced growth characteristics."

Methods for Producing Mammalian Cells Having Enhanced Growth Characteristics

The invention includes methods for producing one or more mammalian cells having enhanced growth characteristics. The methods according to this aspect of the invention comprise performing one or more selection cycles, wherein each selection cycle comprises: (a) subjecting either (i) a starting population of mammalian cells, or (ii) one or more cells obtained in step (b), to selective conditions in which less than 70% of the starting population of cells remain viable; and (b) obtaining one or more mammalian cells that remain viable under the selective conditions.

According to this aspect of the invention, the cells obtained from the selection cycles preferably exhibit an ICA that is at least 25%, at least 30%, at least 35%, at least 40%, at least 45%, at least 50%, at least 55%, at least 60%, at least 65%, at least 70%, at least 80%, at least 85%, at least 90%, or at least 95% greater than the corresponding ICA of the starting population of cells, when the cells obtained from the selection cycles and the starting population of cells are grown under substantially the same culture conditions.

The ICA can be expressed in terms of "X-day ICA." For instance, if the cells are incubated in culture for 2, 3, 4, 5, 6, 7, 8, 9, or 10 days, the ICA may be expressed as the 2-day ICA, 3-day ICA, 4-day ICA, 5-day ICA, 6-day ICA, 7-day ICA, 8-day ICA, 9-day ICA, or 10-day ICA, respectively. The "corresponding ICA of the starting population of cells" is the ICA of the starting population of cells calculated using the same "number of days" parameter that is used to calculate the ICA of the cells obtained from the selection cycles. For example, if the ICA of the cells obtained from the selection cycles is expressed in terms of a "ten-day ICA," then the corresponding ICA of the starting population of cells is the ten-day ICA of the starting population of cells. Likewise, if the ICA of the cells obtained from the selection cycles is expressed in terms of a "five-day ICA," then the corresponding ICA of the starting population of cells is the five-day ICA of the starting population of cells.

Selective conditions in which less than 70% of the starting population of cells remain viable include any culture conditions, selective pressures or manipulations that produce a number of viable cells that is less than 70% of the starting number of cells. Such conditions will be appreciated by persons of ordinary skill in the art and are discussed elsewhere herein.

In order to determine whether a given selective condition is such that less than 70% of the starting population of cells remain viable, a person of ordinary skill in the art could, for example, inoculate a culture medium with a certain number of cells, subject the culture to conditions which are thought to reduce the viability of the cells, and monitor the number of viable cells in the culture over time. Exemplary parameters that can be manipulated to identify selective conditions in which less than 70% of the starting population of cells remain viable include: temperature (e.g., hot or cold temperatures), medium composition (e.g., the presence of components that adversely influence the viability of the cells, e.g., toxic compounds, or the absence of components that are necessary for optimum cell viability), atmospheric pressure, oxygen and $CO_2$ concentrations, pH, osmolality, size of culture (e.g., very large or very small culture volumes), type of culture vessel, amount of time the cells are incubated in the culture, and combinations of any of the aforementioned parameters.

Thus, exemplary selective conditions include but are not limited to: (a) incubating cells in culture media at temperatures of about 40° C., about 45° C., about 50° C., about 55° C., about 60° C., about 65° C., about 70° C., about 75° C., about 80° C., about 85° C., or higher; (b) incubating cells in culture media at temperatures of about 20° C., about 18° C., about 16° C., about 14° C., about 12° C., about 10° C., about 18° C., or lower; (c) incubating cells in culture for extended periods of time (e.g., at least 5, 6, 7, 8, 9, 10, 15, 20, 30, 40, 50, or more days); (d) incubating cells in culture for extended periods of time (e.g., at least 5, 6, 7, 8, 9, 10, 15, 20, 30, 40, 50, or more days) without refreshing or exchanging the medium; (e) incubating cells in medium containing one or more exogenous or endogenous toxic ingredients; (f) incubating cells in medium lacking animal-derived components (e.g., serum, BSA, hydrolysates, etc.); and (g) incubating cells in a medium having a pH outside the optimal pH range for the growth of cells in culture (e.g., a pH of about 0.5, 1.0, 1.5, 2.0, 2.5, 3.0, 3.5, 4.0, 4.5, 5.0, 5.5, 6.0, 6.5, 8.0, 8.5, 9.0, 9.5, or higher).

It has been observed that the viability of cells incubated in a bioreactor decreases over time (see Examples 1 and 3). Accordingly, in certain aspects of the invention, the selective conditions in which less than 70% of the starting population of cells remain viable comprise incubating the cells in a bioreactor. For example, certain embodiments of the invention comprise subjecting a starting population of mammalian cells to one or more selection cycles that comprise incubating the cells in a bioreactor for about 1 to 20 days. The amount of time it takes to achieve less than 70% viability under any set of bioreactor operating conditions can easily be determined by monitoring cell viability in the bioreactor at regular intervals. Several types of bioreactors are known and available in the art. Bioreactors are commercially available from several sources, including, e.g., Sartorius BBI Systems, Inc. (Bethlehem, Pa.), Applikon (Schiedam, The Netherlands), Bellco Glass, Inc. (Vineland, N.J.), Wave Biotech, LLC (Bridgewater, N.J.), Dasgip AG (Jülich, Germany), and New Brunswick Scientific, Co. (Edison, N.J.) and others. Any bioreactor known and available in the art, or constructed using known methods and components, can be used in the practice of the methods of the invention.

"Incubating cells in a bioreactor" includes incubating cells in a bioreactor under standard operating parameters (see Example 1), or under conditions that deviate from such parameters. The bioreactor run can be a batch culture (without the addition of a feed), or a fed-batch culture (the addition of a feed formulation during the run). The bioreactor parameters that can be modified in the context of the methods of the present invention include, e.g., type of medium used, temperature, pH, dissolved $O_2$, agitation, feed times, feed formulation, and length (amount of time) of the run.

The medium that is used when incubating cells in a bioreactor can be any medium that permits the selection of cells having enhanced growth characteristics. In certain embodiments, the medium that is used is a medium that has been optimized for the cultivation of the particular cell line chosen. Media for culturing mammalian cells are well known in the art and are available from, e.g., Sigma-Aldrich Corporation (St. Louis, Mo.), HyClone (Logan, Utah), Invitrogen Corporation (Carlsbad, Calif.), Cambrex Corporation (E. Rutherford, N.J.), JRH Biosciences (Lenexa, Kans.), Irvine Scientific (Santa Ana, Calif.), and others.

In certain aspects of the invention, the selective conditions comprise incubating the cells in a bioreactor for 1 to 10, 1 to 20, 1 to 30, 1 to 40, 1 to 50, 1 to 60, 1 to 70, 1 to 80, 1 to 90, 1 to 100, 5 to 10, 5 to 20, 5 to 30, 5 to 40, 5 to 50, 5 to 60, 5 to 70, 5 to 80, 5 to 90, 5 to 100, or more days. For example, the selective conditions can comprise incubating the cells in a bioreactor for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more days.

In other embodiments, the selective conditions in which less than 70% of the starting population of cells remain viable comprise incubating the cells in a medium lacking or substantially lacking serum and/or insulin and insulin substitutes. The term "insulin" includes insulin from human and non-human animals. "Insulin" also includes zinc insulin (e.g., human zinc insulin) and insulin-related (or insulin-like) growth factors (e.g., IGF-1 and IGF-2), and fusion proteins and derivatives thereof (e.g., LongR$^3$, a fusion protein derived from IGF-1 (Morris and Schmid, *Biotechnol. Prog.* 16:693-697 (2000)). The term "insulin substitute" includes any zinc containing compound which allows cells to grow in chemically defined media lacking insulin. Examples of insulin substitutes include, but are not limited to zinc chloride, zinc nitrate, zinc bromide, and zinc sulfate. (U.S. Pat. No. 6,733, 746). Other insulin substitutes include, e.g., antibodies against the insulin receptor that have insulin agonist activity. (U.S. Pat. No. 4,761,371). A medium "substantially" lacks insulin and insulin substitutes if the medium contains either no insulin and insulin substitutes or an amount of insulin and/or insulin substitutes such that the growth rate of DG44 CHO cells in the medium is 0.20 day$^{-1}$ or less. For example, the methods according to this aspect of the invention include subjecting a starting population of cells to one or more selection cycles that comprise incubating the cells in an insulin-free medium.

In certain aspects of the invention, the selective conditions in which less than 70% of the starting population of cells remain viable do not comprise contacting the cells with a culture medium containing exogenously added ammonia, and/or lactic acid.

The term "subjecting," as used herein, includes but is not limited to contacting a cell with a particular composition (e.g., a culture medium or other solid, liquid or semi-solid substance), physically manipulating a cell (e.g., placing a cell in a bioreactor, pelleting a cell by centrifugation, collecting the cell in a filter, transferring a cell from one culture environment to another, etc.), and/or manipulating the environment surrounding the cell (e.g., adjusting the temperature or chemical composition of the culture medium surrounding the cell).

The methods according to this aspect of the invention can include subjecting a starting population of cells to only a single selection cycle. For example, a starting population of cells can be grown in a bioreactor for a period of time (e.g., 1 to 20 days) such that less than 70% of the starting population of cells remain viable. The viable cells are then obtained (e.g., removed from the bioreactor) and their ICA (e.g., their ten-day ICA) is determined and compared to the corresponding ICA of the starting population of cells (e.g., the ten-day ICA of the starting population of cells). In certain instances, a single selection cycle will yield cells having an ICA that is at least 25% greater than the corresponding ICA of the starting population of cells.

In other instances, it may be desirable to subject the cells to multiple selection cycles (e.g., 1, 2, 3, 4, 5, 6, 7, 8, 9, 10, 11, 12, 13, 14, 15, 16, 17, 18, 19, 20, or more selection cycles). For example, multiple selection cycles may be appropriate when it is desired that the cells obtained from the method have an ICA that is substantially greater (e.g., 50 to 100% greater) than the corresponding ICA of the starting population of cells. Persons of ordinary skill in the art will appreciate when multiple, rather than single, selection cycles are appropriate.

A non-limiting example which illustrates the use of multiple selection cycles is as follows: First, a starting population of cells is incubated in a bioreactor for a period of time (e.g., 1 to 20 days) such that less than 70% of the starting population of cells remain viable. The viable cells are then subjected to a second bioreactor run, e.g., under the same conditions and for the same amount of time as the first bioreactor run. In some instances the operating parameters of subsequent bioreactor runs differ from the operating parameters of the preceding run. The viable cells are then either subjected to additional bioreactor runs, or obtained (e.g., removed from the bioreactor) and their ICA (e.g., ten-day ICA) is determined.

In certain embodiments, a "recovery period" can be included between selection cycles. In the recovery period, the cells obtained from the previous cycle are subjected to culture conditions in which greater than 70% of the starting population of cells remain viable, i.e., culture conditions in which the selection pressure is removed or decreased. In some cases, the recovery period comprises subjecting the cells obtained from the previous cycle to culture conditions in which about 80% to 100% of the starting population of cells remain viable. After the recovery period, the cells are either subjected to another selection cycle, or the cells are obtained (e.g., removed from the bioreactor) and their ICA (e.g., ten-day ICA) is determined.

"Obtaining one or more cells that remain viable under said selective conditions" means removing the viable cells from the selective conditions in which less than 70% of the starting population of cells remains viable, and/or removing the selective pressure from the cells. For example, cells can be "obtained" by filtration or centrifugation. "Obtaining one or more cells that remain viable under said selective conditions" can include separating viable cells from non-viable cells; however, separating viable cells from non-viable cells is not essential to the practice of the methods of the invention.

"Obtaining one or more cells that remain viable under said selective conditions" can include removing cells from the initial culture vessel (e.g., flask or bioreactor) and placing them in a new culture vessel or storage container. "Obtaining one or more cells that remain viable under said selective conditions" may also include removing cells from the initial culture vessel temporarily and placing them back in the same culture vessel.

In certain instances, "obtaining one or more cells that remain viable under said selective conditions" simply involves changing the selective conditions. For instance, if the original selective conditions comprise incubating the cells in a medium containing an ingredient that is depleted over time, "obtaining one or more cells" can be accomplished simply by replenishing the ingredient in the culture. Although, in such instances, the cells are never physically removed from the original culture vessel, for purposes of the present invention, the replenishment of the medium with the depleted ingredient is regarded as "obtaining one or more mammalian cells that remain viable under said selective conditions." In some cases, after replenishing the ingredient, the cells are subjected to one or more additional selection cycles.

The cells obtained from the methods according to this aspect of the invention preferably exhibit an ICA that is at least 25% greater than the corresponding ICA of the starting population of cells. A person of ordinary skill in the art will be able to easily ascertain whether cells obtained from the methods of the invention exhibit an ICA that is at least 25% greater than the corresponding ICA of the starting population of cells. For example, the starting population of cells, prior to being subjected to one or more selection cycles, can be grown under a specific set of culture conditions (e.g., in a specific medium composition, at a specific culture temperature, etc.) for ten days. The initial cell density and the final cell density are measured, and the ten-day ICA of the starting population of cells is calculated according to the following equation: ICA=# days×[(final cell density−initial cell density)/ln(final cell density/initial cell density)]. The ten-day ICA of the cells obtained by the methods of the invention can be determined in a similar manner, using the same or similar culture conditions.

By comparing the ICA of the cells obtained from the methods of the invention (e.g., their ten-day ICA) to the corresponding (e.g., ten-day) ICA of the starting population of cells (when the cells obtained from the methods of the invention and the starting population of cells are grown under substantially the same culture conditions), one of ordinary skill in the art will be able to determine if the ICA of the cells obtained from the methods of the invention is at least 25% greater than the corresponding ICA of the starting population of cells.

The starting population of mammalian cells is any population of two or more mammalian cells. The types of mammalian cells that can be used in the methods of the invention are discussed elsewhere herein. The individual cells within a starting population can have the same or substantially the same phenotypic and/or genotypic characteristics. Alternatively, the individual cells within a starting population can have phenotypic and/or genotypic characteristics that are different from one another; i.e., the starting population of cells may be a mixed population of cells.

The starting population of cells can be cells that are capable of growing in media lacking or substantially lacking insulin and insulin substitutes. The starting population of cells can be cells that are capable of growing in media lacking or substantially lacking serum. A medium "substantially" lacks serum if the medium contains either no serum, or an amount of serum such that the growth rate of DG44 CHO cells in the medium is 0.20 day$^{-1}$ or less. In some embodiments, the starting population of cells are cells that are capable of growing in media lacking or substantially lacking both insulin and insulin substitutes and serum.

In some embodiments of the invention, the starting population of cells are Chinese hamster ovary (CHO) cells or derivatives thereof (e.g., CHO cells that have been adapted to serum-free media). For example, the starting population of cells can be CHO DG44 cells, CHO DG44 cells that have been adapted to serum-free media, and/or CHO DG44 cells that have been adapted to growth in media lacking or substantially lacking insulin and insulin substitutes. The starting population of cells can be CHO-K1 cells, CHO DULX-B11 cells. Other cells that can be used in the context of the invention are discussed elsewhere herein.

According to certain embodiments of the invention, the starting population of cells can contain one or more exogenous nucleic acid molecules encoding one or more polypeptides. Exemplary polypeptides that can be expressed from the exogenous nucleic acid molecules are discussed elsewhere herein. The exogenous nucleic acid molecules can be under the control of a constitutive promoter or under the control of an inducible promoter.

The cells obtained from the methods of the invention may be clonally identical. Alternatively, the cells obtained from the methods of the invention may be clonally distinct. For example, among the cells obtained from the methods of the invention which exhibit an ICA that is at least 25% greater than the corresponding ICA of the starting population of cells, there may be individual cells that contain genotypic variations as compared to other cells obtained by the method. The cells obtained from the methods of the invention are useful for numerous downstream applications whether or not they are clonally identical. Nonetheless, in some embodiments of the invention, the methods further comprise subcloning the cells obtained from the selection cycles. Methods for subcloning mammalian cells are well known in the art.

Methods for Producing Mammalian Cells Having the Ability to Grow in Media Lacking Insulin and Insulin Substitutes The invention also includes methods for obtaining one or more mammalian cells having the ability to grow in media lacking or substantially lacking insulin and insulin substitutes. A number of insulins are known to those of ordinary skill in the art. (Gilman, A. G. et al., Eds., The Pharmacological Basis of Therapeutics, Pergamon Press, New York, 1990, pp. 1463-1495.) The term "insulin" includes zinc insulin (e.g., human zinc insulin) and insulin-related (or insulin-like) growth factors (e.g., IGF-1 and IGF-2). The term "insulin substitute" includes any zinc containing compound which allows cells to grow in chemically defined media lacking insulin. Examples of insulin substitutes include, but are not limited to zinc chloride, zinc nitrate, zinc bromide, and zinc sulfate. A medium "substantially" lacks insulin and insulin substitutes if the medium contains either no insulin and insulin substitutes or an amount of insulin and/or insulin substitutes such that the growth rate of DG44 CHO cells in the medium is 0.20 day$^{-1}$ or less.

The methods according to this aspect of the invention comprise performing one or more selection cycles, wherein each selection cycle comprises: (a) contacting either (i) a starting population of cells that exhibit an average growth rate of less than 0.20 day$^{-1}$ in media lacking or substantially lacking insulin and insulin substitutes, or (ii) one or more cells obtained in step (b), with a culture medium lacking or substantially lacking insulin and insulin substitutes; and (b) isolating one or more cells that remain viable in the medium lacking or substantially lacking insulin and insulin substitutes. The cells obtained from the selection cycles have a growth rate of at least 0.30 day$^{-1}$ in a medium lacking or substantially lacking insulin and insulin substitutes.

The methods according to this aspect of the invention also comprise performing two separate, sequential selection procedures, each selection procedure comprising or more selection cycles. The first selection procedure comprises one or more first selection cycles, wherein each first selection cycle comprises: (a) subjecting either (i) a starting population of mammalian cells, or (ii) one or more cells obtained in step (b), to selective conditions in which less than 70% of the starting population of cells remain viable; and (b) obtaining one or more mammalian cells that remain viable under the selective conditions. The second selection procedure comprises one or more second selection cycles, wherein each second selection cycle comprises: (c) contacting either (i) one or more cells obtained from the one or more first selection cycles, or (ii) one or more cells obtained in step (d), with a culture medium lacking or substantially lacking insulin and insulin substitutes; and (d) obtaining one or more cells that remain viable in the medium lacking or substantially lacking insulin and insulin substitutes. The cells obtained from the second selection cycles have a growth rate of at least 0.30 day$^{-1}$ in a medium lacking or substantially lacking insulin and insulin substitutes.

As used herein, the expression "growth rate" is defined by the following equation:

$$\text{Growth Rate} = \ln(\text{final cell density/initial cell density})/\text{\# days}.$$

The cells obtained from the methods according to this aspect of the invention can have growth rates of at least 0.30 day$^{-1}$, 0.35 day$^{-1}$, 0.40 day$^{-1}$, 0.45 day$^{-1}$, or 0.50 day$^{-1}$, 0.55 day$^{-1}$, 0.60 day$^{-1}$, 0.65 day$^{-1}$, 0.70 day$^{-1}$, 0.75 day$^{-1}$, 0.80 day$^{-1}$, 0.85 day$^{-1}$, 0.90 day$^{-1}$, or more, in media lacking or substantially lacking insulin and insulin substitutes.

According to this aspect of the invention, the cells are contacted with a culture medium lacking or substantially lacking insulin and insulin substitutes for any amount of time up to the time where cell viability of the cells drops to zero. In some embodiments, the cells are contacted with a culture medium lacking or substantially lacking insulin an insulin substitutes for 1 to 20, 1 to 15, 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6 or 4 to 5 days.

The methods according to this aspect of the invention can include subjecting a starting population of cells to only a single selection cycle. For example, a starting population of cells can be contacted with a culture medium lacking or substantially lacking insulin and insulin substitutes for, e.g., ten days. The viable cells are then isolated (e.g., removed from the media) and their growth rate in a medium lacking or substantially lacking insulin and insulin substitutes is calculated. In certain instances, a single selection cycle will yield cells having a growth rate of at least 0.25 day$^{-1}$ in a medium lacking or substantially lacking insulin and insulin substitutes.

In other instances, it may be desirable to subject the cells to multiple selection cycles (e.g., 1, 2, 3, 4, 5, 6, 7, 8, 9, 10, 11, 12, 13, 14, 15, 16, 17, 18, 19, 20, or more selection cycles). For example, multiple selection cycles may be appropriate when it is desired that the cells obtained from the method have a growth rate that is substantially greater than 0.25 day$^{-1}$ in a medium lacking or substantially lacking insulin and insulin substitutes. Persons of ordinary skill in the art will appreciate when multiple, rather than single, selection cycles are appropriate. A non-limiting example which illustrates the use of multiple selection cycles is as follows: First, a starting population of cells is contacted with a medium lacking or substantially lacking insulin and insulin substitutes for a period of time (e.g., 4 to 5 days). The viable cells are then contacted with fresh medium lacking or substantially lacking insulin and insulin substitutes for, e.g., another 4 to 5 days. The viable cells are then either contacted again with a fresh medium lacking or substantially lacking insulin and insulin substitutes, or obtained and tested for growth rate.

In certain embodiments, a "recovery period" can be included between selection cycles or between rounds of selection cycles. In the recovery period, the cells obtained from the previous cycle are incubated in a medium containing insulin and/or insulin substitutes for a period of time (e.g., 1 to 10 days). After the recovery period, the cells are either analyzed for growth rate or subjected to another selection cycle.

"Obtaining one or more cells that remain viable in medium lacking or substantially lacking insulin and insulin substitutes" means removing the viable cells from the medium lacking or substantially lacking insulin and insulin substitutes, and/or replacing the medium with new medium that either contains or lacks insulin and/or insulin substitutes. For example, cells can be isolated by filtration or centrifugation. "Obtaining one or more cells that remain viable in medium lacking or substantially lacking insulin and insulin substitutes" can include separating viable cells from non-viable cells; however, separating viable cells from non-viable cells is not essential to the practice of the methods of the invention.

"Obtaining one or more cells that remain viable in medium lacking or substantially lacking insulin and insulin substitutes" can include removing cells from the culture vessel (e.g., flask or bioreactor) and placing them in a new culture vessel or storage container. "Obtaining one or more cells that remain viable in medium lacking or substantially lacking insulin and insulin substitutes" may also include removing cells from the culture vessel temporarily and placing them back in the same culture vessel containing, e.g., fresh medium lacking or substantially lacking insulin and insulin substitutes.

In certain instances, "obtaining one or more cells that remain viable in medium lacking or substantially lacking insulin and insulin substitutes" simply involves replacing the medium that lacks or substantially lacks insulin and insulin substitutes with fresh medium that also lacks or substantially lacks insulin and insulin substitutes, or with fresh medium that contains insulin and/or insulin substitutes. Alternatively, "obtaining one or more cells that remain viable in medium lacking or substantially lacking insulin and insulin substitutes" can comprise adding insulin and/or one or more insulin substitutes to the culture medium. Although, in such instances, the cells are never physically removed from the original culture vessel, for purposes of the present invention, the replacement of the medium, or the addition of insulin and/or insulin substitutes to the medium, is regarded as "obtaining one or more mammalian cells that remain viable in a medium lacking or substantially lacking insulin and insulin substitutes."

The cells obtained according to this aspect of the invention, although they are able to grow in media lacking or substantially lacking insulin and insulin substitutes, may, in certain embodiments, exhibit improved growth characteristics in media that is supplemented with (a) insulin, (b) one or more insulin substitutes, (c) vanadate, and (d) combinations thereof, as compared to their growth characteristics in media that lacks insulin and insulin substitutes (see Example 2).

The starting population of mammalian cells is any population of two or more mammalian cells. The types of mammalian cells that can be used in the methods of the invention are discussed elsewhere herein. The individual cells within a starting population can have the same or substantially the same phenotypic and/or genotypic characteristics. Alternatively, the individual cells within a starting population can have phenotypic and/or genotypic characteristics that are different from one another; i.e., the starting population of cells may be a mixed population of cells.

The starting population of cells can be cells that have been obtained according to any method described herein. For example, the starting population of cells used in this aspect of the invention can be cells that have been subjected to one or more selection cycles comprising subjecting a starting population of cells to selective conditions in which less than 70% of the starting population of cells remain viable, and isolating one or more cells that remain viable under the selective conditions, wherein the cells obtained from the selection cycles exhibit an ICA that is at least 25% greater than the corresponding ICA of the starting population of cells. By using cells that have been obtained by such methods as a starting population of cells for this aspect of the invention, cells can be obtained that possess both enhanced growth characteristics (faster growth and/or the ability to achieve higher cell density) and the ability to grow in media lacking insulin and insulin substitutes (See Example 2).

According to certain embodiments of the invention, the starting population of cells contain one or more exogenous nucleic acid molecules encoding one or more polypeptides. Exemplary polypeptides that can be expressed from the exogenous nucleic acid molecules are discussed elsewhere herein. The exogenous nucleic acid molecules can be under the control of a constitutive promoter or under the control of an inducible promoter.

Cells Having Enhanced Growth Characteristics and/or the Ability to Grow in Media Lacking Insulin and Insulin Substitutes The invention also includes mammalian cells having enhanced growth characteristics and/or the ability to grow in media lacking insulin and insulin substitutes.

For example, the invention includes one or more isolated CHO cells that exhibit an ICA that is at least 25%, at least 30%, at least 40%, at least 50%, at least 60%, at least 70% or at least 80% greater than the corresponding ICA of DG44 CHO cells, when the isolated CHO cells and the DG44 CHO cells are grown under substantially the same culture conditions. In certain embodiments, the isolated CHO cells according to this aspect of the invention are capable of growing in media lacking or substantially lacking serum and/or insulin and insulin substitutes.

The invention also includes one or more isolated CHO cells that, when incubated in a medium lacking or substantially lacking insulin or insulin substitutes, exhibit an ICA that is at least at least 25%, at least 30%, at least 40%, at least 50%, at least 60%, at least 70% or at least 80% greater than the corresponding ICA of DG44 CHO cells incubated in a medium lacking or substantially lacking insulin or insulin substitutes. In certain embodiments, the isolated CHO cells according to this aspect of the invention are capable of growing in media lacking or substantially lacking serum.

Methods for determining ICA and for comparing the ICA of one population of cells to the corresponding ICA of another population of cells are described elsewhere herein.

The invention also includes one or more isolated cells that, when incubated in a medium lacking or substantially lacking insulin or insulin substitutes, exhibit a growth rate of at least 0.25 day$^{-1}$, 0.30 day$^{-1}$, 0.35 day$^{-1}$, 0.40 day$^{-1}$, 0.45 day$^{-1}$, or 0.50 day$^{-1}$, 0.55 day$^{-1}$, 0.60 day$^{-1}$, 0.65 day$^{-1}$, 0.70 day$^{-1}$, 0.75 day$^{-1}$, 0.80 day$^{-1}$, 0.85 day$^{-1}$, 0.90 day$^{-1}$, or more.

The isolated cells according to this aspect of the invention can be cells that have been obtained by the practice of one or more methods of the present invention. For example, the invention includes one or more isolated mammalian cells having enhanced growth characteristics, wherein the cells are obtained by a method comprising performing one or more selection cycles, wherein each selection cycle comprises: (a) subjecting either (i) a starting population of cells, or (ii) one or more cells obtained in step (b), to selective conditions in which less than 70% of the starting population of cells remain viable; and (b) obtaining one or more mammalian cells that remain viable under the selective conditions; wherein the cells obtained from the one or more selection cycles exhibit an ICA that is at least 25% greater than the corresponding ICA of the starting population of cells, when the cells obtained from the one or more selection cycles and the starting population of cells are grown under substantially the same culture conditions.

The invention also includes one or more mammalian cells having the ability to grow in media lacking or substantially lacking insulin and insulin substitutes, wherein the cells are obtained by a method comprising performing one or more selection cycles, wherein each selection cycle comprises: (a) contacting either a starting population of cells that exhibit a growth rate of less than 0.20 day$^{-1}$ in media lacking or substantially lacking insulin and insulin substitutes, or one or more cells obtained in step (b), with a medium lacking or substantially lacking insulin and insulin substitutes; and (b) obtaining one or more cells that remain viable in media lacking or substantially lacking insulin and insulin substitutes; wherein the cells obtained from the one or more selection cycles have a growth rate of at least 0.25 day$^{-1}$ in a medium lacking or substantially lacking insulin and insulin substitutes.

The isolated cells according to this aspect of the invention can contain one or more exogenous nucleic acid molecules encoding one or more polypeptides. Exemplary polypeptides that can be expressed from the exogenous nucleic acid molecules are discussed elsewhere herein. The exogenous nucleic acid molecules can be under the control of a constitutive promoter or under the control of an inducible promoter.

Mammalian Cells

The mammalian cells of the present invention, including the mammalian cells that are used in or obtained by the methods of the invention, are any mammalian cells that are capable of growing in culture. Exemplary mammalian cells include, e.g., CHO cells (including CHO-K1, CHO DUKX-B11, CHO DG44), VERO, BHK, HeLa, CV1 (including Cos; Cos-7), MDCK, 293, 3T3, C127, myeloma cell lines (especially murine), PC12, HEK-293 cells (including HEK-293T and HEK-293E), PER C6, Sp2/0, NS0 and W138 cells. Mammalian cells derived from any of the foregoing cells may also be used. The mammalian cells of the invention may be adherent cells or cells capable of growing in suspension. The mammalian cells of the invention may contain one or more mutations which confer one or more desired phenotypes (e.g., dihydrofolate reductase deficiency (dhfr$^-$)). The mammalian cells of the invention can be cells that have been adapted to growth under certain conditions such as, e.g., the ability to grow in the media lacking or substantially lacking serum, and/or the ability to grow in medium lacking or substantially lacking insulin and insulin substitutes.

Polypeptides Expressed from Cells of the Invention

Certain embodiments of the invention include cells, and/or methods for producing cells, that contain one or more exogenous nucleic acid molecules encoding one or more polypeptides. An "exogenous nucleic acid molecule" is a nucleic acid molecule that has been introduced into a cell, or a nucleic acid molecule that has been introduced into an ancestor of the cell.

The exogenous nucleic acid molecule can be included within a vector. Exemplary vectors include plasmids, phagemids, cosmids, viruses and phage nucleic acids or other nucleic acid molecules that are able to replicate autonomously or to be replicated in a mammalian cell. Typical expression vectors contain transcription and translation terminators, initiation sequences, and promoters useful for regulation of the expression of the exogenous nucleic acid molecule. The vectors may also comprise genetic expression cassettes containing at least one independent terminator sequence, sequences permitting replication of the vector in both eukaryotes and prokaryotes, i.e., shuttle vectors, and selection markers for both prokaryotic and eukaryotic systems. The vectors preferably contain a marker to provide a phenotypic trait for selection of transformed host cells such as conferring resistance to antibiotics such as ampicillin or neomycin.

The exogenous nucleic acid molecule can be under the control of one or more promoters. For example, the exogenous nucleic acid molecules can be under the control of a constitutive promoter or an inducible promoter. Exemplary promoters include promoters derived from the human cytomegalovirus, metallothionine promoter, SV-40 early promoter, SV-40 later promoter, murine mammary tumor virus promoter, Rous sarcoma virus promoter, polyhedrin promoter, or other promoters shown effective for expression in eukaryotic cells.

Polypeptides that may be encoded by the exogenous nucleic acid molecules include polypeptides of pharmaceutical, medicinal, nutritional, and/or industrial value. The exogenous nucleic acid molecules found within the cells of certain embodiments of the invention can encode, e.g., an enzyme (e.g. β-galactosidase); a hormone; a cytokine; an interleukin; an interferon; TNF; a growth factor (e.g. IGF-1); a soluble receptor molecule (e.g., a soluble TNF receptor molecule); a neurotransmitter or its precursor; a trophic factor such as BDNF, CNTF, NGF, IGF, GMF, aFGF, bFGF, NT3 and NT5; an apolipoprotein such as ApoAI and ApoAIV; dystrophin or a minidystrophin; a tumor-suppressing protein such as p53, Rb, Rap1A, DCC and k-rev; a factor involved in coagulation such as factors VII, VIII and IX; neublastin; or all or part of a natural or artificial in-immunoglobulin (e.g. Fab and ScFv, or the light or heavy chain of a cloned IgG)

The exogenous nucleic acid molecules found within the cells of certain embodiments of the invention can also encode, e.g., a Flt3 ligand, a CD40 ligand, erythropoietin, thrombopoietin, calcitonin, Fas ligand, ligand for receptor activator of NF-kappa B (RANKL), TNF-related apoptosis-inducing ligand (TRAIL), ORK/Tek, thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons (e.g., interferon beta), nerve growth factors, glucagon, interleukins 1 through 18, colony stimulating factors, lymphotoxin-β, tumor necrosis factor, leukemia inhibitory factor, oncostatin-M, various ligands for cell surface molecules Elk and Hek (such as the ligands for eph-related kinases, or LERKS), and antibody light or heavy chains.

The exogenous nucleic acid molecules found within the cells of certain embodiments of the invention can also encode, e.g., a receptor for any of the aforementioned polypeptides, including both forms of tumor necrosis factor receptor (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, BAFF receptor, lymphotoxin beta receptor, TGFβ receptor types I and II, and receptors that include death domains, such as Fas or Apoptosis-Inducing Receptor (AIR).

The exogenous nucleic acid molecules found within the cells of certain embodiments of the invention can also encode, e.g., a polypeptide of the cluster of differentiation antigens (referred to as CD proteins), for example, those disclosed in Leukocyte Typing VI (Proceedings of the VIth International Workshop and Conference; Kishimoto, Kikutani et al., eds.; Kobe, Japan, 1996), or CD molecules disclosed in subsequent workshops. Examples of such molecules include CD27, CD30, CD39, CD40, and ligands thereto (CD27 ligand, CD30 ligand and CD40 ligand). Several of these are members of the TNF receptor family, which also includes 41BB and OX40; the ligands are often members of the TNF family (as are 41BB ligand and OX40 ligand).

The exogenous nucleic acid molecules found within the cells of certain embodiments of the invention can also encode, e.g., metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-I antitrypsin, TNF-alpha Converting Enzyme (TACE), and numerous other enzymes.

The exogenous nucleic acid molecules found within the cells of certain embodiments of the invention can also encode, e.g., immunoglobulin molecules or portions thereof and chimeric antibodies (e.g., an antibody having a human constant region coupled to a murine antigen binding region) or fragments thereof. Numerous techniques are known by which DNAs encoding immunoglobulin molecules can be manipulated to yield DNAs encoding recombinant proteins such as single chain antibodies, antibodies with enhanced affinity, or other antibody-based polypeptides (see, for example, Larrick et al, *Biotechnology* 7:934-938 (1989); Reichmann et al., *Nature* 332:323-327 (1988); Roberts et al., *Nature* 328:731-734 (1987); Verhoeyen et al., *Science* 239:1534-1536 (1988); Chaudhary et al., *Nature* 339:394-397 (1989)). Cloned humanized antibodies include those specifically binding to lymphotoxin beta receptor and integrins such as VLA-1, and VLA-4. Such antibodies can be agonists or antagonists.

The exogenous nucleic acid molecules found within the cells of certain embodiments of the invention can also encode fusion proteins. Exemplary fusion proteins include, e.g., proteins expressed as a fusion with a portion of an immunoglobulin molecule, proteins expressed as fusion proteins with a zipper moiety, and novel polyfunctional proteins such as a fusion proteins of a cytokine and a growth factor (e.g., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins.

In embodiments in which the cells of the invention contain an exogenous nucleic acid molecule encoding a polypeptide, the polypeptide can, in some instances, be isolated and/or purified from the cells using standard techniques in the art. For example, where the exogenous nucleic acid molecule encodes a fusion polypeptide comprising a purification tag, the polypeptide may be purified using antibodies or other compounds that specifically bind to the tag. For example, an oligonucleotide encoding a tag molecule can be ligated at the 5' or 3' end of an exogenous nucleic acid molecule encoding a polypeptide; the nucleic acid molecule may encode a poly-His (such as hexaHis), or other "tag" such as FLAG, HA (hemaglutinin Influenza virus) or myc for which commercially available antibodies or other compounds that specifically bind to the tag are known. This tag is typically fused to the polypeptide upon expression of the polypeptide, and can serve as means for affinity purification of the desired polypeptide from the host cell. Affinity purification can be accomplished, for example, by column chromatography using antibodies against the tag as an affinity matrix. Optionally, the tag can subsequently be removed from the purified polypeptide by various means such as proteolytic cleavage.

Methods for Producing Polypeptides

The present invention also includes methods for producing one or more polypeptides. Any polypeptide, including those described elsewhere herein, can be produced according to this aspect of the invention. The methods according to this aspect of the invention comprise: (a) performing one or more selection cycles, wherein each selection cycle comprises: (i) subjecting either (A) a starting population of cells, or (B) one or more cells obtained in step (ii), to selective conditions in which less than 70% of the starting population of cells remain viable; and (ii) obtaining one or more mammalian cells that remain viable under the selective conditions; (b) introducing a nucleic acid molecule encoding said polypeptide into the cells obtained from the one or more selection cycles; and (c) culturing the cells obtained in (b) under conditions in which the polypeptide is expressed from the nucleic acid molecule. The cells obtained from the one or more selection cycles preferably exhibit an ICA that is at least 25% greater than the corresponding ICA of the starting population of cells when the cells obtained from the one or more selection cycles and the starting population of cells are grown under substantially the same culture conditions.

Methods for introducing a nucleic acid molecule into a cell are well known to those of ordinary skill in the art, including, e.g. infection, transduction, electroporation, transfection, and transformation. Persons of ordinary skill in the art will also appreciate the types of conditions that can be used to culture cells so that a polypeptide is expressed from a nucleic acid molecule. In many instances, the conditions in which the polypeptide is expressed from the nucleic acid molecule comprise simply culturing the cells containing the nucleic acid molecule in a suitable medium. The polypeptide will be produced as cells grow and proliferate in culture. This is especially the case when the nucleic acid molecule is under the control of a constitutive promoter. When the nucleic acid molecule is under the control of an inducible promoter, the conditions in which the polypeptide is expressed comprise, for example, culturing the cells in the presence of the inducible stimulus. The nucleic acid molecule may be under the control of a genetic control element which inhibits expression when a particular substance is present in the medium surrounding the cell. In such cases, the conditions in which the polypeptide is expressed may comprise culturing the cells in the absence of the substance that suppresses expression from the nucleic acid molecule.

The methods according to this aspect of the invention may further comprise treating the cells to cause the polypeptide to be released from the cell. Methods for treating a cell such that a polypeptide, produced therein, is released from the cell, are well known in the art and include, e.g., chemical disruption of the cell and physical disruption of the cell including, e.g., boiling, freezing, grinding, and combinations of chemical and physical disruption of the cell. Such methods include producing a protein extract from the cell.

Once released from the cell, the polypeptide that was encoded from the nucleic acid molecule can be purified using well known techniques. The polypeptide may contain a tag which facilitates the purification of the polypeptide by contacting the tag with an immobilized compound that specifically recognizes and binds to the tag.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Generation of an Evolved DG44 Host Cell Line (DG44(E)) Capable of Higher Peak Cell Density and ICA in a Bioreactor Introduction One way to increase the amount of product obtained from a host cell is to increase the ICA of the host cell. This can be accomplished by increasing the growth rate, increasing the maximal cell density, or delaying the death phase. Increases in ICA can be obtained to some extent through optimization of media, feeds and physiochemical parameters. However, by using a genetic selection approach even greater increases in ICA are possible.

In this example, an approach is described where cells that are resistant to the cell death trigger(s) found in the late stages of the bioreactor process were selected in an attempt to identify cell lines with enhanced growth characteristics. It has been observed that cells stop growing and start dying in fed-batch bioreactor processes. Possible causes of the reduction in viability include nutrient limitations, metabolic waste buildup and changes in osmolarity or redox potential. The present example presents an unbiased selection approach that exposes cells to the "toxic" environment of a bioreactor to select for cells that have enhanced growth characteristics.

Starting with a DG44 CHO cell line that had been adapted to serum-free culture ("SF DG44"), a new host was derived using a process that selected for cells that could survive the environment found in the late stages of a typical fed batch bioreactor nm. In order to obtain this new host, four reiterative bioreactor runs were done where cells were inoculated into a bioreactor, grown using a fed-batch process, collected after the viability had dropped below 50%, allowed to recover, and then used to inoculate the next round. From this process a cell line with a different phenotype was obtained. This new cell line, referred to as DG44(E), was capable of a higher peak cell density and an 82% increase in integral cell area (ICA) when compared to the original SF DG44 host. When tested for transfection efficiency and secretion capacity, DG44(E) was found to be comparable to the original serum-free adapted host.

Materials and Methods

A. Cells

The DG44 cell line is described in Urlaub et al., *Somatic Cell and Molecular Genetics* 12:555-566 (1986) and is available from commercial sources (e.g., Invitrogen Corporation, Carlsbad, Calif.). The cell line used in this example is a DG44 derivative that has been adapted to growth in serum-free media ("SF DG44").

B. Media

Two media were used in the selection protocol. Media 1 was used for passaging and scale-up. Media 2 was used as the basal media in the bioreactor. Feeds were added to the bioreactor on the days indicated in the following table:

| Round # | Feed schedule | Harvest day | Harvest viability |
|---|---|---|---|
| 1 | Days 3, 5, 7 | 10 | 40% |
| 2 | Days 3, 5, 7, 11, 20*, 25* | 35 | 40% |
| 3 | Days 3, 5, 7 | 7 | 45% |
| 4 | Days 3, 5, 7 | 11 | 39% |

*During round 2 fresh media was added instead of feed only on days 20 and 25. On days 20 and 25, 33% and 40% of the total volume was added, respectively.

C. Selection Protocol

The serum-free adapted DG44 cell line (SF DG44) was run in a bioreactor. Cells were sterilely collected daily starting when viability dropped below 50%. The sample from the latest day that was able to grow out was expanded and used to inoculate the next bioreactor run. ICA and growth rates were monitored. After four rounds were completed, the growth characteristics of DG44(E) cells were compared against the original serum-free adapted DG44 cell line. Standard Bioreactor Operating Parameters are as follows:

| Parameter | Setpoint or Strategy |
|---|---|
| Temperature set point | 36° C. |
| pH set point | pH 7.25 (day 0 to day 3); pH 7.00 (day 3 and beyond) |
| Dissolved oxygen (DO) set point | 30% air saturation |
| Agitation | 214 rpm for 2L Braun reactors (65 cm/sec impeller tip speed) |
| DO control | 0.015 vvm air sparge, switch from air to enriched air (40% $O_2$) around day 5 |
| pH control | 1M NaCarbonate and $CO_2$ sparge (0.015 vvm) pH dropped on day 3 with 0.25M HCl |
| Gas overlay | Air at 0.00625 vvm |

D. Transient Transfections and FACS Analysis

Uncut pUC19 (control), pX10 (Test Protein expression), and pE-GFP-C1 (GFP expression) were aseptically resuspended in 1× Hepes Buffered Saline (HeBS: 20 mM Hepes pH 7.05, 137 mM NaCl, 5 mM KCl, 0.7 mM $Na_2HPO_4$, 6 mM dextrose) at concentrations of 1 μg/μL, 1.8 μg/μL, and 2 μg/μL respectively. Plasmids were mixed together at various concentrations (see below) in a final volume of 800 μL of 1×HeBS.

| Transfection # | DNA concentrations |
|---|---|
| 1, 10 | 100 μg pUC19 |
| 2, 3, 4, 5, 11, 12, 13, 14 | 100 μg pX10 plus 20 μg pE-GFP-C1 |
| 6, 7, 8, 9, 15, 16, 17, 18 | 200 μg pX10 plus 20 μg pE-GFP-C1 |

After centrifugation, $2\times10^6$ cells were resuspended in 800 μL of DNA/1×HeBS mixture and transferred to a Biorad 0.4 cm gap electroporation cuvette. Settings used on the Biorad Gene Pulser were 0.28 Kv and 950 μFd (capacitance extender is necessary). Pulsed cells were allowed to rest in the cuvette for 10 minutes prior to being spun down in 10 mL of α+ MEM (Gibco #11900-024) supplemented with 10% Fetal Bovine Serum (Hyclone#SH30070.03). Each transfection was plated onto one 10 cm dish in 3 mL of α+ MEM plus 10% serum. After three days supernatant was harvested for assay by HPLC (Test Protein expression) and cells were harvested for FACS analysis (GFP expression).

E. Assays

An HPLC Protein-A assay was employed for analyzing the 72 hr. conditioned media samples from the transient transfection experiment.

F. Calculations

Total cell densities were determined by Coulter Counter and viabilities were determined by trypan blue exclusion and hemacytometer counting. Viable cell densities, growth rates, and integral cell area (ICA) were determined using the formulas below.

Viable cells/mL=(total cells/mL) (% viability/100).

Growth Rate=ln(final cell density/initial cell density)/# days.

ICA=# days×[(final cell density−initial cell density)/ln (final cell density/initial cell density)].

Results and Discussion

A. Selection Protocol

Starting with the serum-free adapted DG44 host (also referred to as "regular"), reiterative bioreactor runs were performed. Each round showed an increased peak cell density and consequently an increased ICA. After four rounds of bioreactor selection the DG44(E) host achieved a peak cell density of $2.7\times10^6$ with a ten-day ICA of $1.4\times10^7$. The starting cell line achieved a peak cell density of $1.3\times10^6$ and a ten-day ICA of $7.8\times10^6$. This represents a 107% increase in peak cell density and an 82% increase in ICA over the starting cell line (FIG. 1). The viability of the "evolved" cells was comparable to the original cells throughout the process (data not shown).

TABLE I

| Cell Type | Specific Productivity Picograms/cell/day | pX10 DNA |
|---|---|---|
| Regular | 0.45 +/− 0.11 | 100 μg |
| Evolved | 0.60 +/− 0.11 | |
| Regular | 1.85 +/− 0.14 | 200 μg |
| Evolved | 1.64 +/− 0.24 | |

B. Transient Transfections and FACS Analysis

After each selective run the evolved cells seemed to be getting smaller (by viewing in hemacytometer). It may be that smaller cells fair better in the bioreactor due to greater shear resistance. Having noticed that the "evolved" cells were smaller in size than their original counterparts, secretion ability became a concern. However, titer results from a transient transfection experiment showed no differences in secretory potential between the DG44(E) cell line and the DG44 SF host (Table I). FACS scans on cells transiently transfected with Green Fluorescent Protein (GFP) also showed no differences in transfection efficiency between the DG44(E) cell line and the starting host cell line (Table II).

TABLE II

| Cell type | % GFP Positive | pX10 DNA |
|---|---|---|
| Regular | 46% +/− 4% | 100 μg |
| Evolved | 59% +/− 3% | |
| Regular | 51% +/− 5% | 200 μg |
| Evolved | 58% +/− 4% | |

Example 2

Generation of an Insulin Independent DG44 CHO Host Cell Line (DG44-I)

Introduction

Insulin is the most commonly used growth factor in serum-free CHO media formulations. It is also the most expensive media component in these formulations and can represent >50% of the media/feed cost in a fed-batch process.

A new host cell called DG44-I was derived from the serum free adapted DG44(E) CHO host cell line (see Example 1). DG44-I can grow in the absence of insulin. This adaptation was achieved in four passages using insulin free media. The new host has a growth rate of approximately 0.65 days' in insulin-free media. The DG44-I host has been successfully transfected. The DG44-I host is still responsive to insulin in that exposure to insulin results in a modest increase in growth rate.

Figure 2:
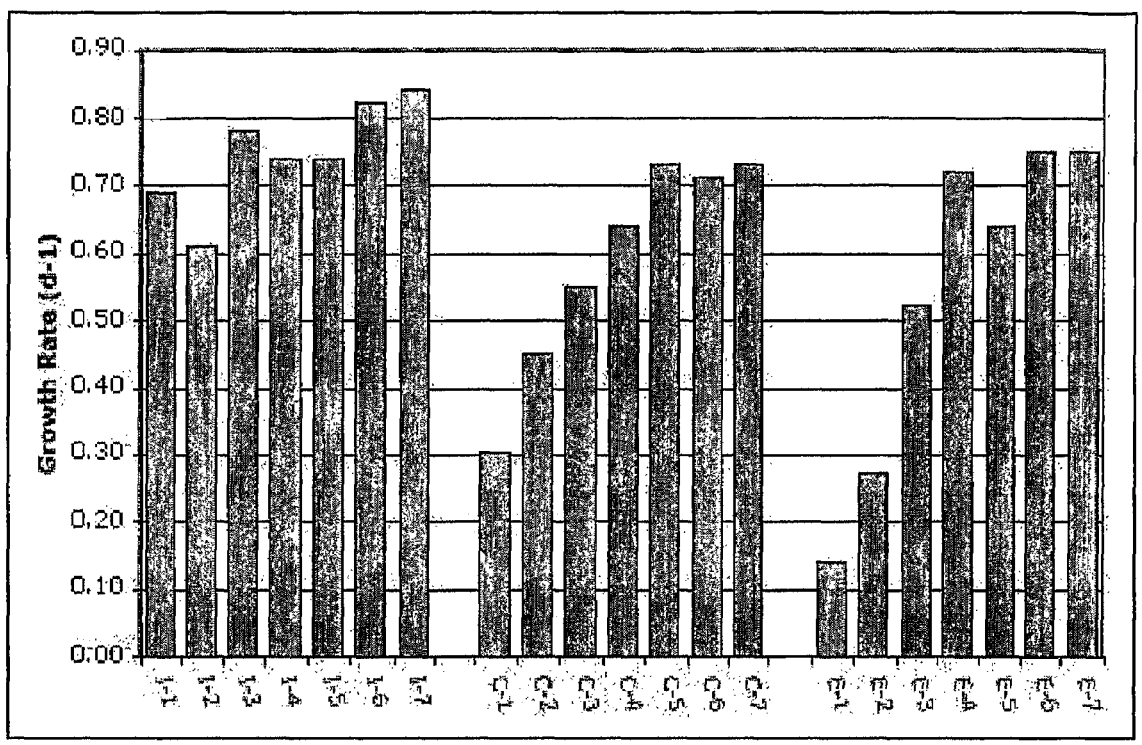
FIG. 2 is a bar graph showing the growth rate of DG44(E) cells after successive passaging in media either with or without insulin. Seven passages from the point of insulin removal are shown for the two DG44-I lineages, C and E. The I series is the same host passaged in media containing 5 mg/mL recombulin Zn.
Figure 3:
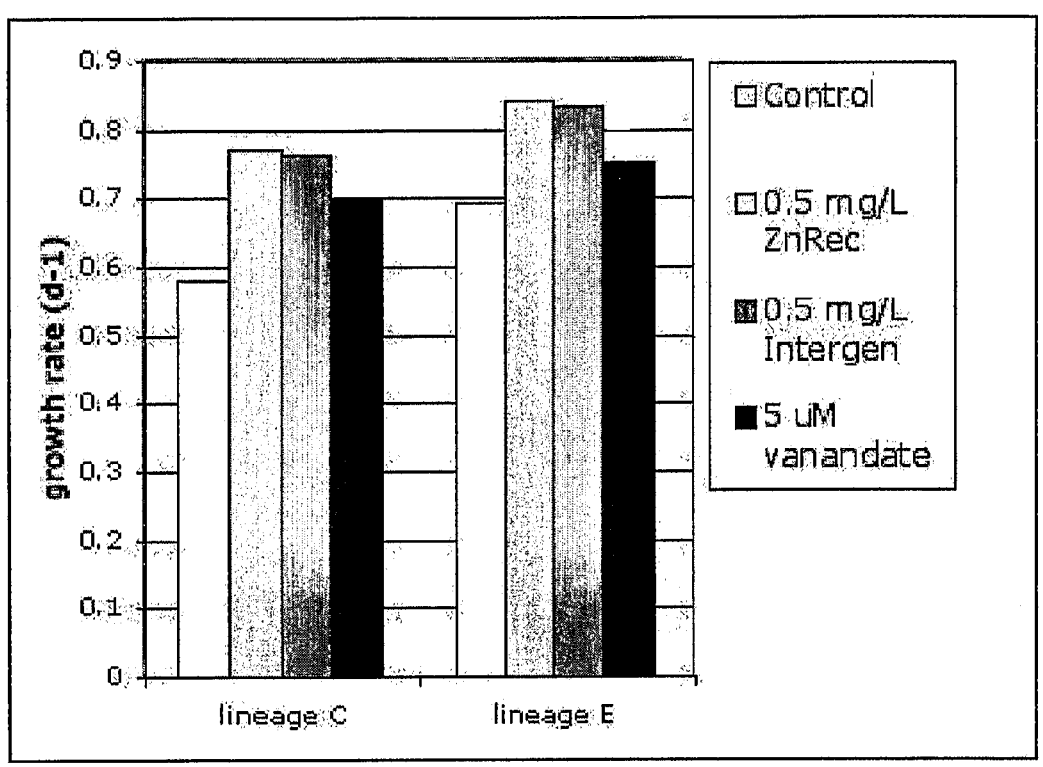
FIG. 3 is a bar graph showing the effect of insulin (recombulin Zn or Intergen insulin) and vanadate on the growth rate of DG44-I cells (lineages C an E). The growth rates were based on a three day passage, where the insulin or vanadate was added at the beginning of the passage. Control represents no insulin or vanadate.

Materials and Methods
  A. Cells and Media
  The DG44 cell line is described in Urlaub et al., *Somatic Cell and Molecular Genetics* 12:555-566 (1986) and is available from commercial sources (e.g., Invitrogen Corporation, Carlsbad, Calif.). The DG44(E) cell line was obtained by the method described in Example 1. DG44(E) cells can be routinely passaged to $1 \times 10^5$ vc/mL in media supplemented with nucleosides. The DG44-I host can be passaged in the same media with or without insulin.
  B. Vanadate
  When prepared correctly, sodium orthovanadate will be clear and colorless. If the solution has a slight orange-yellow color to it this indicates the presence of vanadate polyanion, which is not optimal. In order to avoid the formation of polyanion large pH changes should be avoided. The method described in Kadota et al., *J. Biol. Chem.* 262:8252-8256 (1987) is as follows. A bicarbonate/HEPES buffer (118.5 mM NaCl, 4.7 mM KCl, 2.5 mM $CaCl_2$, 1.2 mM $KH_2PO_4$, 1.2 mM $MgSO_4$, 24.9 nM $NaHCO_3$, 30 mM HEPES) adjusted to pH 6.8 with HCl was prepared. Sodium orthovanadate was added to this buffer to a concentration of 5 mM which raises the pH somewhat. The pH was then adjusted to 7.4 with NaOH and the solution was filter sterilized.
  C. Selection Protocol
  The DG44-I host was derived from the DG44(E) host by successive passaging in a serum-free medium without insulin. In the first passage the insulin was removed by media exchange and a PBS wash. The cells underwent a complete media exchange every three to four days for the next three passages. After the fourth passage the cells had achieved growth rates $>0.6$ $d^{-1}$ and were passaged by splitting to $1 \times 10^5$-$2 \times 10^5$ viable cells/mL every three to four days. After a total of eight passages, the cells were used to generate a small bank of 16 vials.
  D. Growth Rates
  Growth rates were determined using the formula below:
  Growth Rate=ln(final cell density/initial cell density)/# days.
Results and Discussion
  The approach used to generate the DG44-I host was to remove the insulin in a single step. The rationale behind this approach was based on previous work where some transfectants were shown to be insulin independent. If a substantial fraction of the DG44(E) host was insulin independent, then perhaps a "cold turkey" approach might work here as well. The fact that a growth rate $>0.6$ $days^{-1}$ was achieved in less than five passages supports this notion.
  A. Selection
  Multiple paths of insulin independent growth were initiated in the first passage. Of these, two were carried for eight passages and frozen. Lineage C was originally seeded at $1.1 \times 10^5$ vc/mL and lineage E was originally seeded at $3 \times 10^5$ vc/mL. After the first passage these two lineages were passaged in a similar manner.
  The viability in lineage C never dropped below 90% during those eight passages. The viability in lineage E was 78% at the end of the first passage, 89% at the end of the second passage and >90% at the end of all the subsequent passages. These results suggest that the DG44(E) host was not highly dependent on insulin.
  Both lineages suffered a modest drop in growth rate in the first passage (FIG. 2). Over the course of the subsequent passages the growth rate increased to a level that is comparable to the DG44(E) host in media containing insulin. After passage four the growth rate leveled off between 0.6 and 0.75 $day^{-1}$. Since this growth rate is more than adequate for the host, the cells were used to generate a small bank after passage eight.
  B. Response to Insulin and Vanadate
  Even though the DG44-I host can grow in the absence of insulin, it is still responsive to insulin. The host is also responsive to vanadate ($V_2O_5$), which is a phosphate analog that can act as an insulin "enhancing" agent in animals and cell culture (Shechter et al., *Mol. Cell. Biochem.* 153:39-47 (1995)). Cells from passage from both the C and E lineages were seeded into serum-free medium with nucleosides and without insulin containing either 0.5 mg/L Recombulin Zn, 0.5 mg/L Intergen insulin, 5 µM vanadate, or no addition (FIG. 3). In each case, the addition of insulin or vanadate resulted in an increase in growth rate in the first three days. When these cultures were carried out to seven days, there were no obvious differences (data not shown). This growth rate "turbo boost" may be useful in some applications. It is not known if the effect would last beyond one passage
  C. Transfection
  The DG44-I host (lineage E) has been used for a number of transfections. In these transfections, no notable differences were observed in either transfection efficiency or productivity of the screened cell lines.

Example 3

Application of "Bioreactor Evolution" to Increase ICA and Throughput in a CHO Cell Line Expressing a Test Protein
Introduction
  A new CHO cell line expressing a Test Protein (CHO/Test) was derived using the "Bioreactor Evolution" process. Bioreactor Evolution is a process that selects for cells that can survive the environment found in the late stages of the bioreactor process (see Example 1). In order to obtain this new cell line, three reiterative bioreactor runs were done where cells were inoculated into a bioreactor, grown under standard bioreactor conditions, collected after the viability had dropped below 40%, allowed to recover, and then used to inoculate the next round. From this method a cell line with a new phenotype was obtained. This new cell line, referred to as CHO/Test(E), was capable of a higher peak cell density, a 29% increase in integral cell area (ICA), and a 34% increase in throughput when compared to the CHO/Test cell line (Table IV). When product quality was examined, CHO/Test (E) was found to be comparable to the CHO/Test cell line.
Materials and Methods
  A. Cells
  The CHO/Test cell line is a CHO DUKX-B11-derived cell line containing a transgene which expresses the Test Protein.
  B. Media
  Two media were used in the selection protocol. Media 3 was used for passaging and scale-up. Media 4 was used as the basal media in the bioreactor. Feeds were added to the bioreactor on the days indicated in the following table:

| Round # | Feed schedule | Harvest day | Harvest viability |
|---|---|---|---|
| 1 | Days 2, 4, 5, 7 | 10 | 11% |
| 2 | Days 2, 4, 5, 7 | 9 | 32% |
| 3 | Days 2, 4, 5, 7 | 11 | <10% |

C. Selection Protocol
  The CHO/Test cell line was run in a bioreactor. Cells were sterilely collected daily starting when viability dropped below 40%. The sample from the latest day that was able to grow out was expanded and used to inoculate the next bioreactor rm. ICA, growth rates, and specific productivities were monitored. After three rounds were completed, the CHO/Test (E) cells were run against the CHO/Test control cells. The bioreactor parameters used are as follows:

| Parameter | Setpoint or Strategy |
|---|---|
| Temperature set point | 37° C. |
| pH set point | pH 7.4 |
| Dissolved oxygen (DO) set point | 30% air saturation |
| Agitation | 214 rpm for 2L Braun reactors (65 cm/sec impeller tip speed) |
| DO control | 0.015 vvm air sparge, switch from air to enriched air (40% $O_2$) around day 5 |
| pH control | 0.5 molal NaCarbonate and $CO_2$ sparge (0.015 vvm) |
| Gas overlay | Air at 0.0125 vvm |

D. Assays

An HPLC Protein-A assay was employed for determining total Test Protein titer. An HPLC Protein-A assay was used to determine percent aggregation and monomer titer. Product quality was assessed by Isoelectric Focusing and carbohydrate profile.

E. Calculations

Total cell densities were determined by Coulter Counter and viabilities were determined by trypan blue exclusion and hemacytometer counting. Viable cell densities, growth rates, specific productivities, and ICA were determined using the formulas below.

Viable cells/mL=(total cells/mL)(% viability/100)

Growth Rate=ln(final cell density/initial cell density)/# days

ICA=# days×[(final cell density-initial cell density)/ln(final cell density/initial cell density)]

Bioreactor Throughput=(mg/L)/(No. days for bioreactor process and turnaround time)

Results and Discussion

A. Selection Protocol

Figure 4:
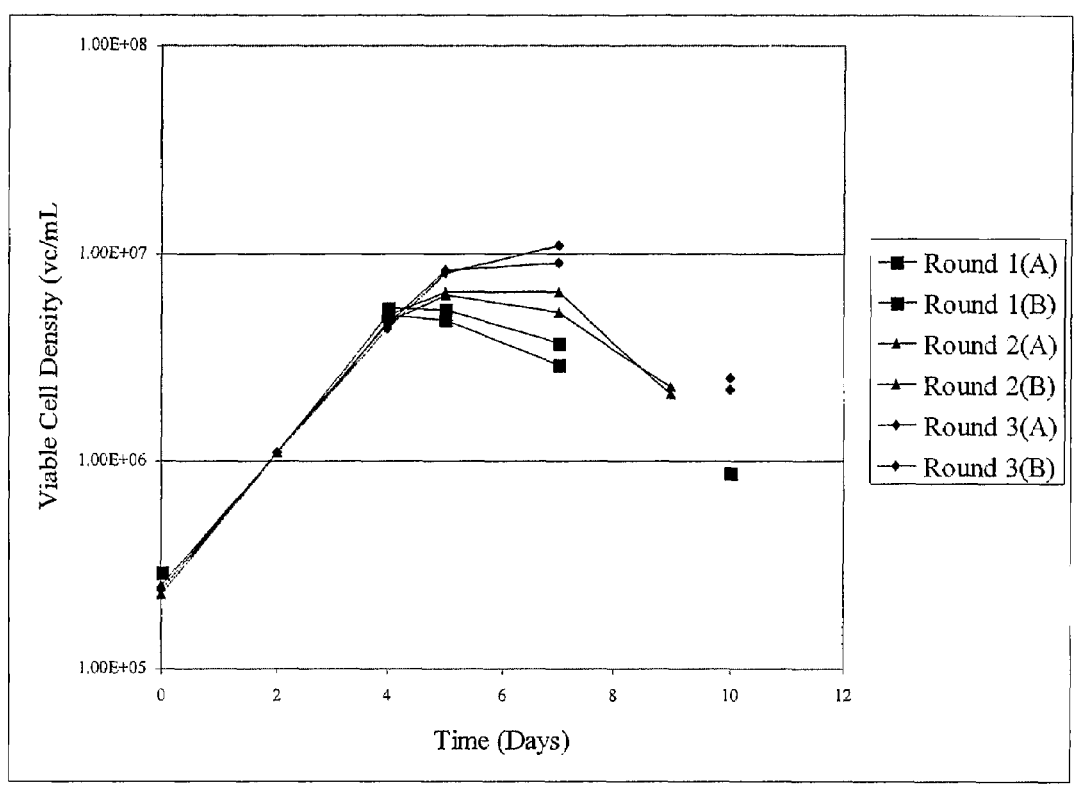
FIG. 4 is a graph showing the viable cell density (vc/mL) of derivatives of the CHO/Test cell line obtained from three reiterative bioreactor runs (Rounds 1, 2 and 3), as a function of time. Two samples from each run (A and B) were tested.
Figure 5:
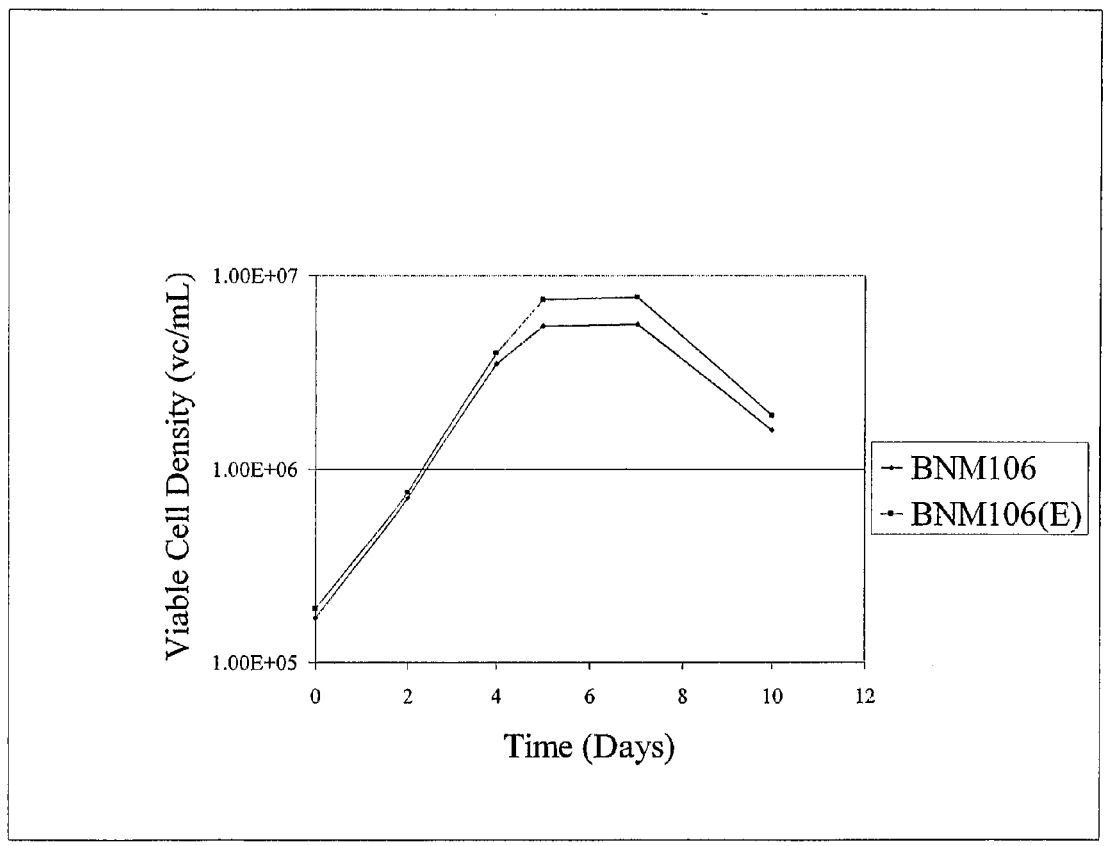
FIG. 5 is a graph comparing the viable cell density (vc/mL) of the CHO/Test starting cell line to the viable cell density of the CHO/Test(E) cell line (obtained from the bioreactor evolution process), as a function of time in a fed-batch process.

Starting with the CHO/Test cell line, three reiterative bioreactor runs were performed. Each round showed an increased peak cell density and consequently an increased ICA (FIG. 4). After three rounds of bioreactor selection the CHO/Test (E) cell line achieved a peak cell density of $7.7 \times 10^6$ vc/mL with a 7-day ICA of $2.6 \times 10^7$ cells/mL/day in a head-to-head comparison to CHO/Test (FIG. 5). This represents a 38% increase in peak cell density, a 29% increase in ICA, and a 34% increase in throughput over the CHO/Test cell line control (Table III).

TABLE III

CHO/Test vs CHO/Test(E), Growth, Titer and Throughput

|  | CHO/Test | CHO/Test(E) | % Increase |
|---|---|---|---|
| Peak Cell Density (vc/mL) | $5.6 \times 10^6$ | $7.7 \times 10^6$ | 38 |
| Integral Cell Area (vc/mL/Day) | $1.98 \times 10^7$ | $2.55 \times 10^7$ | 29 |
| Titer (mg/L) | 138 | 188 | 36 |
| Monomer Titer (mg/L) | 140 | 188 | 34 |
| Throughput (mg/L/Day) | 15.6 | 20.9 | 34 |

When the product quality of Test Protein produced by CHO/Test(E) was examined, it was found to be comparable to that of the CHO/Test control (Tables IV-IX).

TABLE IV

Throughput in milligrams/Liter/Day (Harvest Monomer Titer/9 [7-day process plus 2 days turnaround time])

|  | Evolved CHO/Test | CHO/Test control |
|---|---|---|
| Day 6 |  |  |
| Day 7 | 20.9 | 15.6 |
| Day 8 |  |  |
| Day 10 | 17.8 | 13.4 |

TABLE V

Specific Productivity (picograms/cell/day)

|  | Evolved CHO/Test | CHO/Test control |
|---|---|---|
| Day 5 | 5.4 | 8.6 |
| Day 6 |  |  |
| Day 7 | 7.4 | 7 |
| Day 10 | 6.1 | 5.4 |

TABLE VI

Percent Aggregation

|  | Evolved CHO/Test | CHO/Test control |
|---|---|---|
| Day 5 |  |  |
| Day 6 |  |  |
| Day 7 | 6.8% | 6.2% |
| Day 8 |  |  |
| Day 10 | 7.2% | 6.1% |

TABLE VII

Total Percent Sialic Acid

|  | Evolved CHO/Test | CHO/Test control |
|---|---|---|
| Day 5 |  |  |
| Day 6 |  |  |
| Day 7 | 81.55% | 80.97% |
| Day 8 |  |  |
| Day 10 | 77.66% | 77.66% |

TABLE VIII

IEF

|  | Evolved CHO/Test | CHO/Test control |
|---|---|---|
| Day 7 | Compares favorably | Compares favorably |
| Day 10 | Compares favorably | Compares favorably |

TABLE IX

Percent Glycan Distribution

|  | Day | Evolved CHO/Test | CHO/Test control |
|---|---|---|---|
| TetraLac-NaX | Day 7 | 5.48% | 3.8% |
| Tetra-NaX | Day 7 | 27.5% | 23.7% |
| Tri-NaX | Day 7 | 19.39% | 18.54% |
| Bi-NaX | Day 7 | 23.35% | 28.66% |

TABLE IX-continued

| | Percent Glycan Distribution | | |
|---|---|---|---|
| | Day | Evolved CHO/Test | CHO/Test control |
| Bi-1Gal | Day 7 | 10.44% | 10.58% |
| Bi-2Gal | Day 7 | 13.55% | 14.18% |

Conclusion

This example demonstrates that it is possible to take an already transfected cell line and, by subjecting it to bioreactor evolution, increase the throughput of the bioreactor process without compromising the product quality of the expressed protein. Bioreactor Evolution can be an alternative approach to increasing ICA and throughput if media development or other process changes are not favorable. Due to the selective nature of "bioreactor evolution" it is probable that the CHO/Test(E) population generated is not a homogenous one. A subcloning following the "evolution" might be useful for pulling out cell lines capable of an even higher throughput than what was achieved.

Having now Sully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for producing one or more Chinese hamster ovary (CHO) cells having enhanced growth characteristics, said method comprising:
   (a) subjecting a starting population of CHO cells to one or more selection cycles comprising selective conditions; wherein said selective conditions comprise incubating said cells in a bioreactor in which less than 70% of said starting population of cells remain viable, with the proviso that said selective conditions do not comprise contacting said cells with a culture medium containing exogenously added ammonium;
   (b) obtaining one or more CHO cells that remain viable under said selective conditions;
   wherein said cells obtained from said one or more selection cycles exhibit all integral cell area (ICA) that is at least 25% greater than the corresponding ICA of said starting population of cells when said cells obtained from said one or more selection cycles and said starting population of cells are grown under the same culture conditions; and
   (c) inoculating said cells obtained in (b) into a bioreactor.

2. The method of claim 1, wherein said selective conditions comprise incubating said cells in a bioreactor for 1 to 100 days.

3. The method of claim 2, wherein said selective conditions comprise incubating said cells in a bioreactor for 5 to 50 days.

4. The method of claim 3, wherein said selective conditions comprise incubating said cells in a bioreactor for 5 to 30 days.

5. The method of claim 3, wherein said selective conditions comprise incubating said cells in a bioreactor for 5 to 20 days.

6. The method of claim 1, wherein said selective conditions comprise incubating said cells in a bioreactor for an amount of time such that less than 60% of said starting population of cells remain viable.

7. The method of claim 1, wherein said selective conditions comprise incubating said cells in a bioreactor for an amount of time such that less than 50% of said starting population of cells remain viable.

8. The method of claim 1, wherein said selective conditions comprise incubating said cells in a bioreactor for an amount of time such that less than 40% of said starting population of cells remain viable.

9. The method of claim 1, wherein said bioreactor is run under fed-batch conditions.

10. The method of claim 1, wherein said bioreactor is run under batch-mode conditions.

11. The method of claim 1, wherein said incubating is in a medium lacking or substantially lacking insulin and insulin substitutes.

12. The method of claim 1, wherein said starting population of cells is subjected to 1 to 20 of said selection cycles.

13. The method of claim 12, wherein said starting population of cells is subjected to 1 to 10 of said selection cycles.

14. The method of claim 13, wherein said starting population of cells is subjected to 1 to 5 of said selection cycles.

15. The method of claim 14, wherein said starting population of cells is subjected to 1 to 4 of said selection cycles.

16. The method of claim 15, wherein said starting population of cells is subjected to 3 or 4 of said selection cycles.

17. The method of claim 1, wherein said selective conditions are conditions in which between 5% and 50% of said starting population of cells remain viable after said one or more selection cycles.

18. The method of claim 17, wherein said selective conditions are conditions in which between 10% and 50% of said starting population of cells remain viable after said one or more selection cycles.

19. The method of claim 18, wherein said selective conditions are conditions in which between 20% and 50% of said starting population of cells remain viable after said one or more selection cycles.

20. The method of claim 19, wherein said selective conditions are conditions in which between 30% and 50% of said starting population of cells remain viable after said one or more selection cycles.

21. The method of claim 1, wherein said starting population of cells are capable of growing in media lacking or substantially lacking insulin and insulin substitutes.

22. The method of claim 1, wherein said starting population of cells are capable of growing in media lacking or substantially lacking serum.

23. The method of claim 1, wherein said starting population of cells contain one or more exogenous nucleic acid molecules encoding one or more polypeptides.

24. The method of claim 23, wherein one or more of said exogenous nucleic acid molecules is under the control of a constitutive promoter.

25. The method of claim 23, wherein one or more of said exogenous nucleic acid molecules is under the control of an inducible promoter.

26. The method of claim 23, wherein one or more of said polypeptides is an antibody or fragment thereof.

27. The method of claim 1, wherein said CHO cells are CHO DG44 cells.

28. The method of claim 1, wherein said CHO cells are CHO DUKX-B11 cells.

29. The method of claim 1, wherein said CHO cells are CHO-K1 cells.

30. The method of claim 29, wherein said CHO DG44 cells are capable of growing in media lacking or substantially lacking serum.

31. The method of claim 27, wherein said CHO DG44 cells contain one or more exogenous nucleic acid molecules encoding one or more polypeptides.

32. The method of claim 31, wherein one or more of said exogenous nucleic acid molecules is under the control of a constitutive promoter.

33. The method of claim 31, wherein one or more of said exogenous nucleic acid molecules is under the control of an inducible promoter.

34. The method of claim 1, wherein between said selection cycles, said cells are subjected to a recovery period comprising incubating said cells in the absence of said selective conditions.

35. A method for producing a polypeptide, said method comprising:
(a) introducing a nucleic acid molecule encoding the polypeptide into one or more cells obtained by the method of claim 1; and
(b) culturing said cells containing said nucleic acid molecule under conditions in which said polypeptide is expressed from said nucleic acid molecule.

36. The method of claim 1, wherein said cells obtained from said one or more selection cycles exhibit an ICA that is at least 50% greater than the corresponding ICA of said starting population of cells when said cells obtained from said one or more selection cycles and said starting population of cells are grown under the same culture conditions.

37. The method of claim 1, wherein said cells obtained from said one or more selection cycles exhibit an ICA that is at least 70% greater than the corresponding ICA of said starting population of cells when said cells obtained from said one or more selection cycles and said starting population of cells are grown under the same culture conditions.

38. The method of claim 1, wherein said cells obtained from said one or more selection cycles have a growth rate of at least 0.30 day$^{-1}$ in a medium lacking or substantially lacking insulin and insulin substitutes.

39. The method of claim 1, wherein said method further comprising subcloning said cells obtained from said one or more selection cycles.

40. A method for producing one or more Chinese hamster ovary (CHO) cells having the ability to grow in media lacking or substantially lacking insulin and insulin substitutes, said method comprising:
(a) performing a first round of selection comprising:
(i) subjecting a starting population of CHO cells to one or more selection cycles comprising selective conditions; wherein said selective conditions comprise incubating said cells in a bioreactor in which less than 70% of said starting population of cells remain viable;
(ii) obtaining one or more CHO cells that remain viable under said selective conditions;
(b) performing a second round of selection comprising:
(iii) contacting one or more cells obtained from said first round of selection cycles with a culture medium lacking or substantially lacking insulin and insulin substitutes; and
(iv) obtaining one or more cells that remain viable in said medium lacking or substantially lacking insulin and insulin substitutes;

wherein said cells obtained from said second round of selection have a growth rate that is at least 0.30 day$^{-1}$ in a medium lacking or substantially lacking insulin and insulin substitutes: and
(c) inoculating said cells obtained in (b) into a bioreactor.

41. The method of claim 40, wherein said selective conditions comprise incubating said cells in a bioreactor for 1 to 50 days.

42. The method of claim 40, wherein said CHO cells are CHO DG44 cells.

43. The method of claim 40, wherein said CHO cells are CHO DUKX-B11 cells.

44. The method of claim 40, wherein said CHO cells are CHO-K1 cells.

45. The method of claim 41, wherein said selective conditions comprise incubating said cells in a bioreactor for 5 to 50 days.

46. The method of claim 45, wherein said selective conditions comprise incubating said cells in a bioreactor for 5 to 30 days.

47. The method of claim 46, wherein said selective conditions comprise incubating said cells in a bioreactor for 5 to 20 days.

48. The method of claim 40, wherein said selective conditions comprise incubating said cells in a bioreactor for an amount of time such that less than 60% of said starting population of cells remain viable.

49. The method of claim 48, wherein said selective conditions comprise incubating said cells in a bioreactor for an amount of time such that less than 50% of said starting population of cells remain viable.

50. The method of claim 49, wherein said selective conditions comprise incubating said cells in a bioreactor for an amount of time such that less than 40% of said starting population of cells remain viable.

51. The method of claim 40, wherein said bioreactor is run under fed-batch conditions.

52. The method of claim 40, wherein said bioreactor is run under batch-mode conditions.

53. The method of claim 40, wherein said starting population of cells is subjected to 2 to 20 of said first selection cycles.

54. The method of claim 53, wherein said starting population of cells is subjected to 2 to 10 of said first selection cycles.

55. The method of claim 54, wherein said starting population of cells is subjected to 2 to 5 of first said selection cycles.

56. The method of claim 55, wherein said starting population of cells is subjected to 2 to 4 of first said selection cycles.

57. The method of claim 56, wherein said starting population of cells is subjected to 3 or 4 of first said selection cycles.

58. The method of claim 40, wherein said selective conditions are conditions in which between 5% and 50% of said starting population of cells remain viable after said selection rounds.

59. The method of claim 58, wherein said selective conditions are conditions in which between 10% and 50% of said starting population of cells remain viable after said selection rounds.

60. The method of claim 59, wherein said selective conditions are conditions in which between 20% and 50% of said starting population of cells remain viable after said selection rounds.

61. The method of claim 60, wherein said selective conditions are conditions in which between 30% and 50% of said starting population of cells remain viable after said selection rounds.

62. The method of claim 40, wherein said starting population of cells are capable of growing in media lacking or substantially lacking serum.

63. The method of claim 40, wherein said starting population of cells contain one or more exogenous nucleic acid molecules encoding one or more polypeptides.

64. The method of claim 63, wherein one or more of said exogenous nucleic acid molecules is under the control of a constitutive promoter.

65. The method of claim 63, wherein one or more of said exogenous nucleic acid molecules is under the control of an inducible promoter.

66. The method of claim 63, wherein one or more of said polypeptides is an antibody or fragment thereof.

67. The method of claim 40, wherein between said selection cycles in step (a) and said selection cycle in step (b), said cells are subjected to a recovery period comprising incubating said cells in the absence of said selective conditions.

* * * * *